United States Patent [19]

Toner et al.

[11] Patent Number: 4,933,070

[45] Date of Patent: Jun. 12, 1990

[54] HEMISPHERANDS IN ION-SELECTIVE COMPOSITIONS

[75] Inventors: John L. Toner, Webster; Daniel S. Daniel, Rochester, both of N.Y.

[73] Assignee: Eastman Kodak Company, Rochester, N.Y.

[21] Appl. No.: 873,017

[22] Filed: Jun. 11, 1986

Related U.S. Application Data

[63] Continuation of Ser. No. 496,739, May 20, 1983, abandoned, which is a continuation-in-part of Ser. No. 332,904, Dec. 21, 1981, abandoned.

[51] Int. Cl.$^5$ .............................................. G01N 27/30
[52] U.S. Cl. .................................................... 204/418
[58] Field of Search ......................... 204/417, 418, 1 A

[56] References Cited

U.S. PATENT DOCUMENTS

| | | | |
|---|---|---|---|
| 3,562,129 | 2/1971 | Simon | 204/418 |
| 3,598,868 | 8/1971 | Cram et al. | 562/429 |
| 3,657,095 | 4/1972 | Tosteson | 204/409 |
| 3,743,588 | 7/1973 | Brown et al. | 204/403 |
| 3,753,887 | 8/1973 | Kedem et al. | 204/417 |
| 3,856,649 | 12/1974 | Genshaw et al. | 204/418 |
| 3,957,607 | 5/1976 | Simon et al. | 204/182.4 |
| 3,965,116 | 6/1976 | Cram | 549/348 |
| 4,001,279 | 1/1977 | Cram | 549/348 |
| 4,043,979 | 8/1977 | Cram | 525/332.2 |
| 4,080,337 | 3/1978 | Cram | 260/244.4 |
| 4,113,959 | 9/1978 | Cram | 560/38 |
| 4,128,556 | 12/1978 | Cram | 546/26 |
| 4,134,798 | 1/1979 | Pinsky | 204/1 T |
| 4,214,968 | 8/1980 | Battaglia et al. | 204/418 |
| 4,227,003 | 10/1980 | Debono et al. | 548/216 |
| 4,236,987 | 12/1980 | Schindler et al. | 204/417 |
| 4,263,115 | 4/1981 | Kessler | 204/418 |

FOREIGN PATENT DOCUMENTS

| | | | |
|---|---|---|---|
| 2924285 | 11/1981 | Fed. Rep. of Germany | 549/348 |
| 137080 | 11/1978 | Japan | 549/348 |
| 151994 | 11/1979 | Japan | 549/348 |
| 13502 | 3/1981 | Japan | 549/348 |
| 24571 | 3/1981 | Japan | 549/348 |

OTHER PUBLICATIONS

Renewal Proposal for ERDA Contract AT(04-3)34, P.A. 218—Jan. 15, 1977, pp. 1-22.
ERDA Contract Renewal Proposal for 1978-1979, pp. 2-19.
Renewal Proposal for DOE Contract AT(04-3)34, P.A. 218—pp. 2-17 (1979-1980).
Renewal Proposal for DOE EY 76-S-03-0034, P.A. 218, pp. 2-18, 25-28 (1981-1982).
Third Progress Report for ERDA Contract AT(-04-3)34, P.A. 218, pp. 1-20, Jan. 15, 1977.
Seventh Progress Report for Division of Basic Energy Sciences, Dept. of Energy, Contract DOE EY 76-S-0-3-0034, P.A. 218, pp. 1-13, 1/15/81.
"Concept, Structure, and Binding in Complexation", *Topics in Current Chemistry*, 98, pp. 43-106 (1981).
J. Am. Chem. Soc., 101, pp. 3545-3566, Jun. 1979.
J. Chem. Soc., Chemical Communications, pp. 948-950 (1979).
J.A.C.S., 101, pp. 6752-6754, Oct. 1979.
J.A.C.S., 103, pp. 6228-6232 (1981).
J. Org. Chem., 44, No. 14, pp. 2538-2550 (1979).
J.A.C.S., 101, pp. 4928-4941, Aug. 1979.
Cram., D. J., Science, vol. 219, No. 4589, pp. 1177-1183, Mar. 11, 1983.
Shono et al., J. Electroanal. Chem., vol. 132, pp. 99-105 (1982).
E. Pretsch et al., Research/Development Magazine, vol. 25, No. 3, pp. 20-23, Mar. 1974.
Izatt & Christensen, "Synthetic Multidentate Macrocyclic Compounds", Ed., Academic Press, N.Y., 1978.
Chemical Abstracts 92:198377u (1980).
Research Proposal Submitted to the Division of Physical Research, U.S. Atomic Energy Commission, Washington, D.C. 20545.
Renewal Proposal for AEC Contract AT(04-3)34, P.A. 218—Jan. 15, 1975—pp. 1-13.
Renewal Proposal for ERDA Contract AT(04-3)34, P.A. 218—Jan. 15, 1976—pp. 1-14.
Fourth Progress Report for ERDA Contract AT(-04-3)34, P.A. 218, 1-24.
Fifth Progress Report for Division of Basic Energy Sciences, Dept. of Energy, Contract AT(04-3)34, P.A. 218, pp. 1-25.
"III. Research Results Obtained for the Reporting Period May 1, 1979 through Apr. 30, 1980", pp. 5-19.
J. Chem. Soc. Chem. Comm., pp. 958-959 (1976).
J.A.C.S. 99, pp. 3880-3882, May 1977.
J. Org. Chem. 44, pp. 2226-2233, 1979.
J.A.C.S. 103, pp. 3929-3931, 1981.
J.A.C.S. 98, pp. 4018-4020, Jun. 1976.

*Primary Examiner*—G. L. Kaplan
*Attorney, Agent, or Firm*—J. Jeffrey Hawley

[57] ABSTRACT

Ion-selective compositions which comprise an ion carrier, a compound capable of solvating the ion carrier, and a supporting matrix are disclosed. The ion carrier according to the invention is a lipophilic hemispherand compound. These compositions are particularly useful in ion-selective electrodes. Such an electrode is capable of selectively transporting a first ion in preference to a second ion. Particularly useful hemispherands have a ΔG of complexation with the first ion which is at least 0.3 Kcal/mole greater than the ΔG of complexation with the second ion. Dry-operative electrodes using these ion-selective compositions as membranes are also disclosed.

22 Claims, No Drawings

HEMISPHERANDS IN ION-SELECTIVE COMPOSITIONS

RELATED APPLICATIONS

This is a continuation of Ser. No. 496,739, filed May 20, 1983, and now abandoned, which in turn was a continuation-in-part of Ser. No. 332,904, filed December 21, 1981 and now abandoned. This application is cross referenced in U.S. Ser. No. 496,740, filed on May 20, 1983 entitled HEMISPHERANDS AND SODIUM-SELECTIVE COMPOSITIONS AND ELECTRODES CONTAINING SAME now U.S. Pat. No. 4,476,007. This application is also cross referenced in U.S. Ser. No. 496,738, filed on May 20, 1983 entitled SODIUM-SELECTIVE COMPOSITIONS AND ELECTRODES CONTAINING SAME now U.S. Pat. No. 4,505,800.

FIELD OF THE INVENTION

This invention relates to compositions which are useful as ion-selective membranes. In one particularly preferred embodiment, the compositions are used as ion-selective membranes which are capable of selectively transporting a first ion in preference to a second ion. These membranes are useful in ion-selective electrodes of various types.

DESCRIPTION RELATIVE TO THE PRIOR ART

In the diagnosis and treatment of various diseases as well as in preventative health checkups, it is becoming increasingly important to monitor the concentrations of certain ions (e.g. cations) in a patient's body. Cations which have merited considerable attention in the diagnosis and treatment of heart disease, manic depressive psychosis, kidney disease, diabetes and hypertension are alkali metal ions, e.g. lithiu, sodium and potassium.

A great variety of electrodes and structures for the measurement of such ions in solution are known. Usually, but not necessarily, they include a reference electrode and a separate ion-selective electrode. When these two electrodes are simultaneously immersed in the same sample of a solution containing such ions, a potential develops across a membrane between the electrodes, which potential is proportional to the concentration of the ion to which the ion-selective electrode is sensitive. Frequently, it is desirable to measure the concentration of one ion in preference to other ions which may be in solution. In that case, the ion-selective composition of the ion-selective electrode must be capable of selectively transporting the first ion across the membrane in preference to all other ions. An electrode having this capability is often referred to in the art as an ion-selective electrode.

One type of ion-selective electrode has an electrode body (usually a glass container) containing a reference solution in contact with a half-cell of known potential (a reference electrode) and an ion-selective glass membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the glass membrane. This type of electrode is referred to in the art as a "barrel" electrode.

In addition to the glass membranes, polymeric ion-selective membranes are also known. These membranes generally comprise a polymeric binder or support as the supporting matrix which is impregnated with a solution of an ion-selective carrier in a carrier solvent. The ion-selective carrier is a compound which is capable of sequentially complexing the desired ion, transporting the ion through the composition and releasing the ion. This compound is also referred to in the art as an "ionophore" or "ion carrier". Depending upon the ionophore, solvent and binder, membranes of this type can be used to detect a particular ion preferentially to other ions which may be in the solution.

A significant advance in the ion-selective-electrode art is the dry-operative electrode described in U.S. Pat. No. 4,214,968 (issued July 29, 1980 to Battaglia et al.). Prior to the discovery of such dry-operative ion-selective electrodes, electrodes had to be either stored in an aqueous solution or treated with aqueous solution just prior to use in an ion-activity-determining operation. The term "dry-operative" refers to an ion-selective electrode which provides reproducible potentiometric determination of ion activity which is related to the ion concentration of an aqueous test solution with no requirement for wet storage or preconditioning prior to use.

One of the specific ion-selective electrodes disclosed in the examples of Battaglia et al is a sodium ion-selective electrode using methyl monensin as the sodium-selective ionophore. While methyl monensin is a useful ion-selective membrane for a variety of purposes, still further improvements, particularly in the selectivity of the electrode for sodium over potassium, are desired. For example, methyl monensin is useful in the determination of sodium in blood serum because blood serum usually contains a relatively low level of potassium. However, a higher degree of selectivity of sodium over potassium is needed for the uncorrected determination of sodium in urine and certain other biological fluids because they generally either contain widely fluctuating concentrations of potassium and sodium ions or have more potassium ions than sodium ions.

There are relatively few classes of compounds which are known to be useful in ion-selective compositions. Further, many of the compounds which are known to be ion-selective are naturally occurring compounds which are expensive and difficult to isolate. It is apparent that there is a continuing need for new ion-selective compositions. It is particularly advantageous if this new class of ion-selective compositions contains compounds which are highly selective for certain ions in solution.

SUMMARY OF THE INVENTION

It has now been found that compounds known as hemispherands are useful ionophores in ion-selective compositions. These compositions comprise a lipophilic hemispherand compound, a compound capable of solvating the hemispherand, and a supporting matrix. The composition is useful as an ion-selective membrane. The composition is capable of complexing an ion from solution, transporting the ion from one side of a membrane to another side of a membrane, and releasing the compound to a second solution. In certain embodiments, the hemispherands act as highly selective ionophores and are capable of transporting one ion across a membrane in preference to a second ion in the solution. The fact that hemispherands are useful in the described ion-selective compositions is particularly surprising because extremely closely related compounds, namely, the sperands, do not function as ion-selective compounds in the same manner as is shown in the comparative example.

In accordance with the present invention, there is provided a composition comprising a lipophilic hemispherand compound, a compound capable of solvating the hemispherand and a supporting matrix. This composition is useful as an ion-selective membrane.

In preferred embodiments, the solvating compound is a hydrophobic carrier solvent and the supporting matrix is a hydrophobic binder.

In preferred embodiments of the present invention, there is provided an ion-selective membrane composition capable of selectively transporting a first ion in preference to a second ion, said composition comprising a lipophilic hemispherand, a compound capable of solvating the hemispherand and a supporting matrix, wherein the hemispherand has a ΔG of complexation with the first ion which is at least 0.3 kcal/mole greater than the ΔG of complexation with the second ion.

The compositions described above are also useful in ion-selective electrodes. Thus, in another aspect of the present invention, there is provided an ion-selective electrode having an ion-selective membrane composition comprising an ionophore which is a lipophilic hemispherand compound, a compound capable of solvating the hemispherand compound and a supporting matrix.

The compositions herein are also useful in dry-operative ion-selective electrodes. Thus, in still another aspect of the present invention there is provided a dry-operative ion-selective electrode comprising a lipophilic hemispherand ionophore dissolved in a compound capable of solvating the hemispherand compound.

DETAILED DESCRIPTION OF THE INVENTION

Generically, hemispherands and related compounds are compounds which were first developed by Dr. D. J. Cram and his coworkers (see *Journal of the American Chemical Society*, 101:22, October, 1979, and 101:13, June, 1979; *J. C. S. Chem. Comm.*, page 948, 1979). Hemispherands and closely related spherands are compounds which are known to be capable of complexing ions. We have discovered that, unlike many types of compounds which are capable of binding ions, hemispherands have properties which make them useful as ion carriers or ionophores in a supporting matrix, along with a solvating compound to provide mobility. The closely related spherand compounds do not have these necessary properties.

A hemispherand is a macrocyclic compound wherein at least a portion of the macrocyclic ring contains contiguous rigid cyclic units, at least some of these units having coordinating sites for ions. The rigid cyclic units are sufficient in number to rigidize a portion of the macrocyclic ring structure. The coordinating sites in the cyclic units are oriented so as to face the interior of the macrocycle, thereby forming the rigidized portion of the cavity in the molecule for receiving ions. Hemispherands are distinguished from known crown ethers and cryptands (other classes of macro- cyclic compounds known to bind ions) in that they are structurally much more rigid than these other binding compounds. Crowns and cryptands change conformation during complexation. Hemispherands and spherands, on the other hand, owe their binding capacity to an at least partially rigidized cavity which is lined by rigidized groups capable of forming coordinate bonds with the ion to be bound. Because the cavity is at least partially rigidized, there is reduced configurational change on complexation. The term "spherand" is reserved for those compounds wherein the entire macrocyclic ring structure consists of contiguous rigid cyclic units. In a hemispherand, the portion of the macrocyclic ring structure which is not made up of contiguous rigid cyclic units is made up of any other unit or units, but preferably these other units also contain coordinating sites.

By the term "rigid cyclic unit" is meant a cyclic structure having a coordinating group in or appended to one position on the ring wherein the cyclic unit is connected to the macrocyclic structure through bonds adjacent the coordinating-site position. This connecting bond-coordinating site-connecting bond structure limits the freedom of the cyclic unit to move, i.e., rotate or fold, in the molecule. If three or more of these units are in contiguous positions in the macrocyclic structure, that portion of the macrocyclic structure is rigidized because the freedom of each cyclic unit to move is substantially eliminated. Furthermore, this structure, having the coordinating site between and adjacent the connecting bonds, serves to rigidly orient the coordinating sites toward the interior of the macrocycle.

Useful rigid cyclic units having coordinating sites are derived from compounds such as anisole, methoxycyclohexane, pyridine, pyrimidine, pyridine oxide, pyrimidine oxide, tetrahydropyrimidine, hexahydropyrimidine, hexahydro-2-oxopyrimidine, cyclic urea, benzoquinone, cyclohexanone, cyclic sulfoxides, cyclic phosphine oxides, cyclic amides, cyclic sulfones, furan, tetrahydrofuran, thiophene and tetrahydrothiophene.

Lipophilic hemispherands are hemispherands which contain no solubilizing groups such as carboxylic acid groups or sulfonic acid groups, or which contain sufficiently large oil-soluble groups to render the molecule oil-soluble, e.g., capable of forming a 4%-by-weight solution of the hemispherand in a hydrophobic organic solvent.

In particularly preferred embodiments, the lipophilic hemispherand is represented by the structural formula:

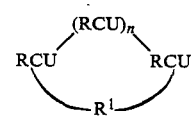

wherein n is an integer of from 1 to 3; each RCU is a rigid cyclic unit individually selected from the group consisting of units of the structure:

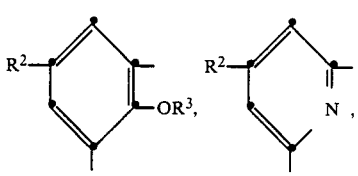

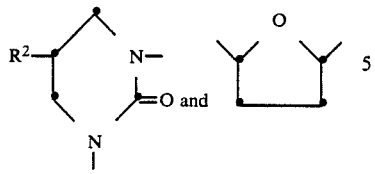

wherein $R^2$ is hydrogen or a group selected from alkyl, preferably containing from 1 to 12 carbon atoms such as methyl, ethyl and isopropyl; alkenyl, preferably containing from 2 to 12 carbon atoms such as allyl, vinyl and 1-propenyl; cycloalkyl, preferably containing from 3 to 10 carbon atoms, such as cyclopropyl and cyclohexyl; aryl such as phenyl including substituted phenyl such as tolyl, xylyl and methoxyphenyl and such groups containing hetero-atoms or containing heteroatom substituents such as dimethylamino, nitro, methoxy and sulfonyl methyl; $R^3$ is an alkyl or alkenyl group such as those defined for $R^2$ or, when taken together with an $R^3$ group from another RCU, forms an alkylene group preferably of about 1 to 10 carbon atoms such as methylene, ethylene, propylene, tetramethylene or such groups interrupted with hetero atoms such as oxydiethylene and oxydipropylene; and $R^1$ represents the atoms necessary to complete a macrocyclic ring structure, preferably having from 16 to 30 atoms in the backbone of the ring structure, with the proviso that $R^1$ contains (a) at least one coordinating site for ions and (b) at least two alkylene groups as part of the ring structure. Useful $R^1$ groups include heteroatom substituted alkylene, such as carbonyloxy-ester substituted ethylene; oxybis(alkylene) such as oxybis(ethylene), oxybis(ethyleneoxymethylene) and oxybis(ethyleneoxyethylene); alkyleneoxyalkyleneoxyalkylene, such as methyleneoxyethyleneoxymethylene; arylene di(oxyalkylene), such as 1,4-dimethyl-5,6-oxymethylene; and groups containing one or more RCU groups such as 2,6-pyridylenebis(methyleneoxymethylene), 2-methoxy-5-methyl-1,3-phenylenebis(methyleneoxymethylene) and 1,10-phenanthroline-2,9-ylenebis(methyleneoxymethylene). Preferably, n is 1 or 2.

Examples of hemispherands within the scope of this structure include:

HS 1-4

HS 1: 3,3″-oxybis(ethyleneoxymethylene)-2,2′, 2″-triethoxy-5,5′,5″-trimethyl-1,1′:3′,1″-terphenyl HS 4: 3,3″-oxybis(ethyleneoxymethylene)-2,2″-ethoxy-2′-propoxy-5,5′,5″-trimethyl-1,1′:3′,1″-terphenyl

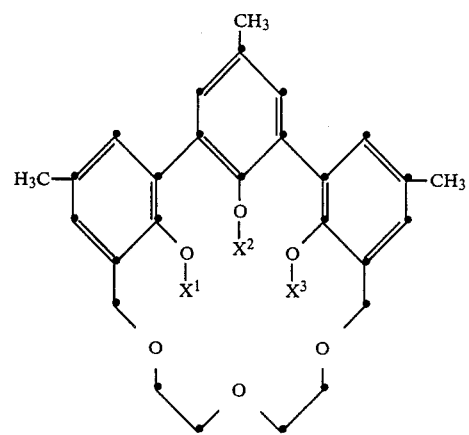

HS 1: $X^1$, $X^2$, $X^3$ = ethyl

HS 2: $X^1$, $X^2$, $X^3$ = propyl

HS 3: $X^1$, $X^2$, $X^3$ = isopropyl

HS 4: $X^1$ and $X^3$ = ethyl and $X^2$ = propyl

HS-5

HS 5: 3,3″-oxybis(ethyleneoxymethylene)-2′-methoxy-2,2″-trimethylenedioxy-5,5′,5″-trimethyl-1,1′:3′,1″-terphenyl

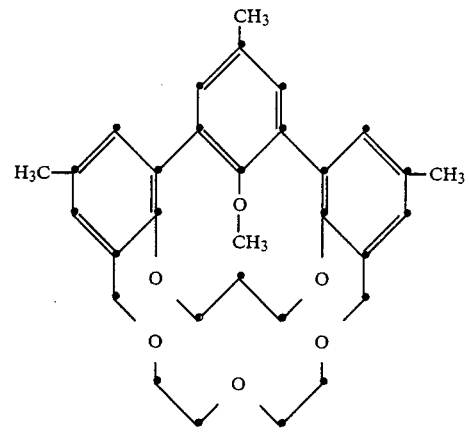

HS 6-7

HS 6: 3,3″-oxybis(ethyleneoxymethylene)-2,2″-tetramethylenedioxy-2′-propoxy-5,5′,5″-trimethyl-1,1′:3′1″-terphenyl HS 7: 3,3″-oxybis(ethyleneoxymethylene)-2,2″-tetramethylenedioxy-2′-allyloxy-5,5′,5″-trimethyl-1,1′:3′1″-terphenyl

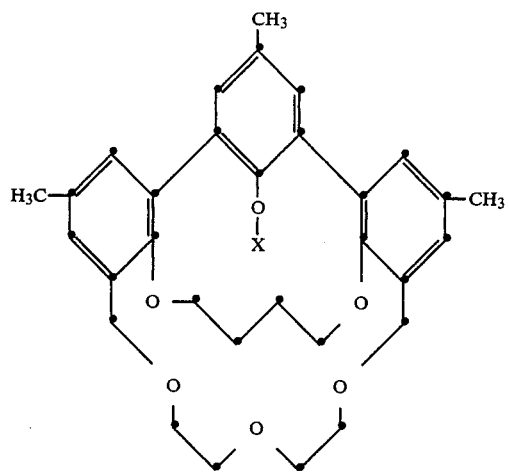
HS 6: X=propyl
HS 7: X=allyl
HS 8-9
HS 8: 3,3''-(2,6-pyridylene)bis(methyleneoxymethylene)-2,2',2''-triethoxy-5,5',5''-trimethyl-1,1':3',1''-terphenyl
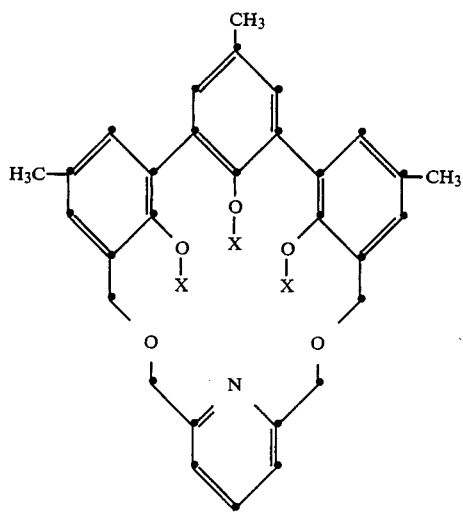
HS 8: X=ethyl
HS 9: X=methyl
HS-10
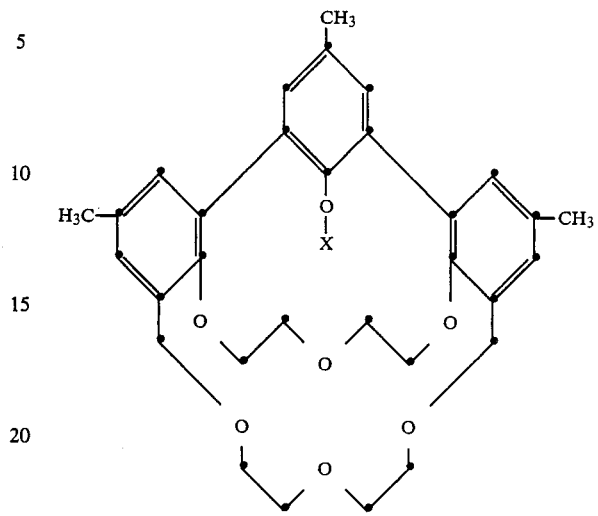
X=allyl
HS-11
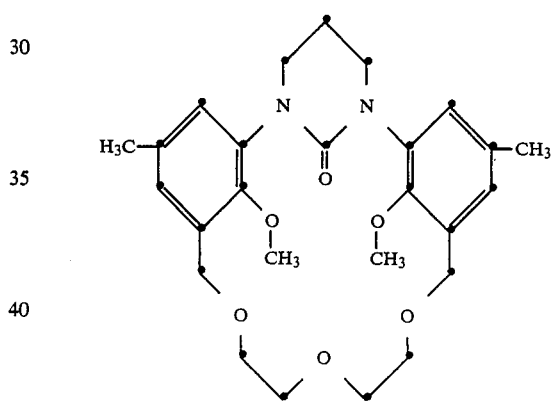
HS-12
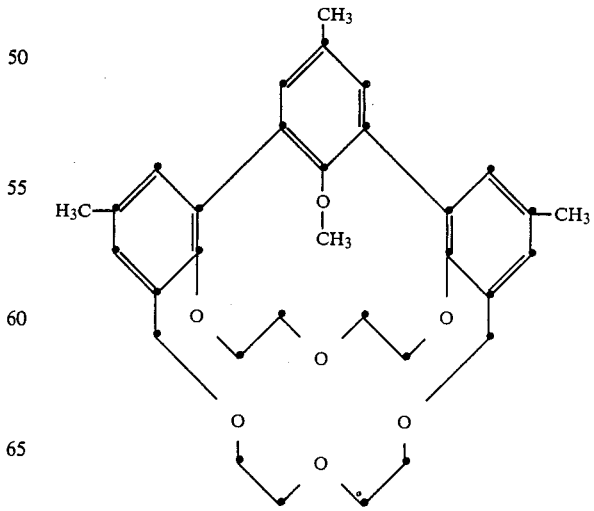

HS-13
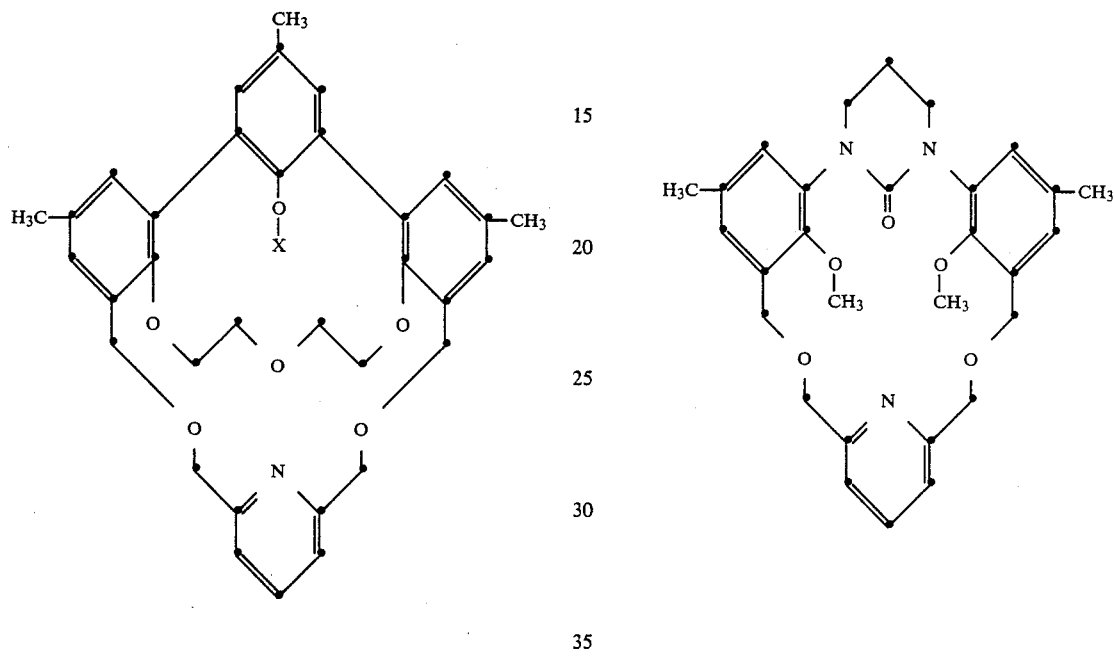
X=allyl
HS-14
HS-15
HS-16
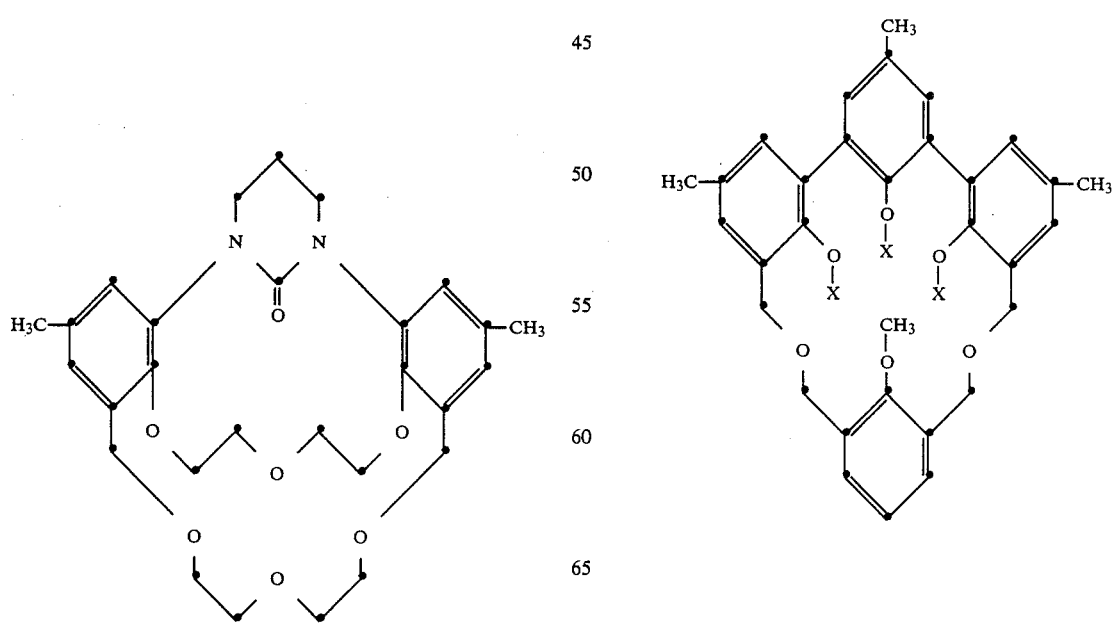
X=ethyl

HS-17
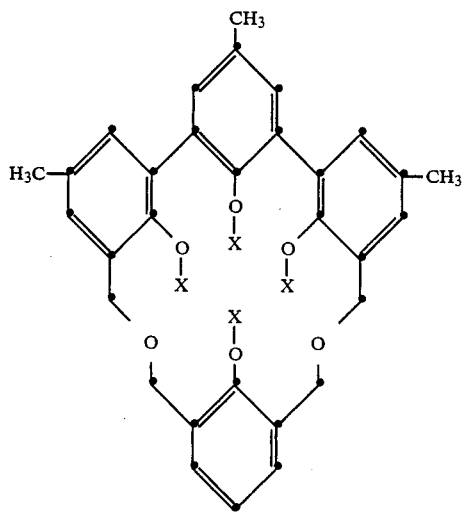
X=ethyl
HS 18-19
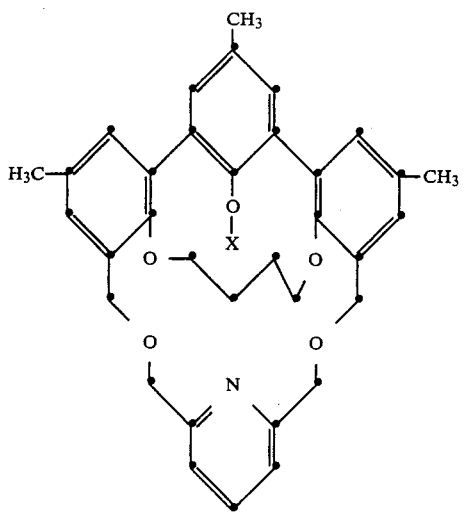
HS 18: X=allyl
HS 19: X=ethyl
HS-20
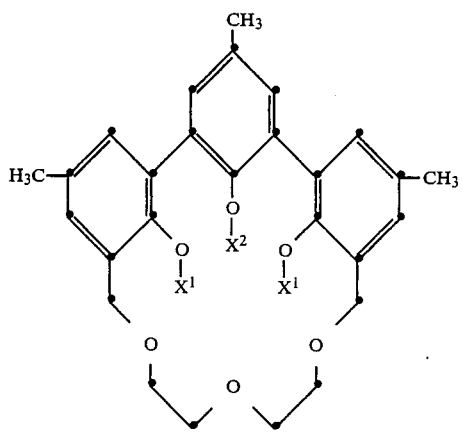
$X^1$=propyl
$X^2$=ethyl
HS-21
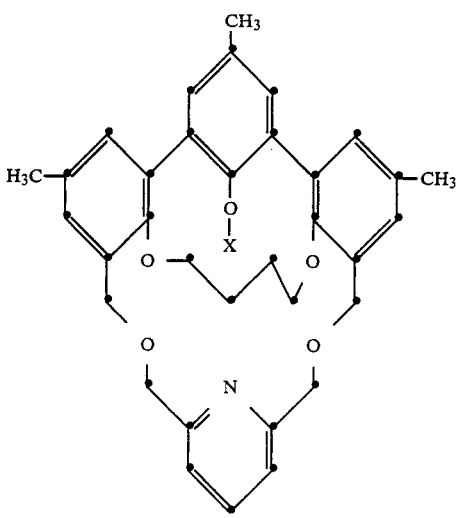
X=CH$_2$C$_6$H$_5$ HS-22
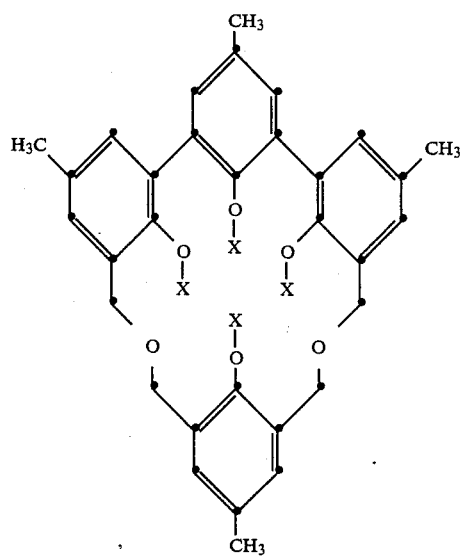
X=methyl
HS-23
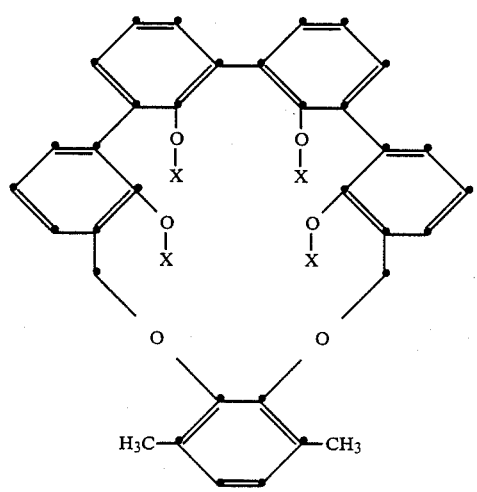
X=methyl
HS-24
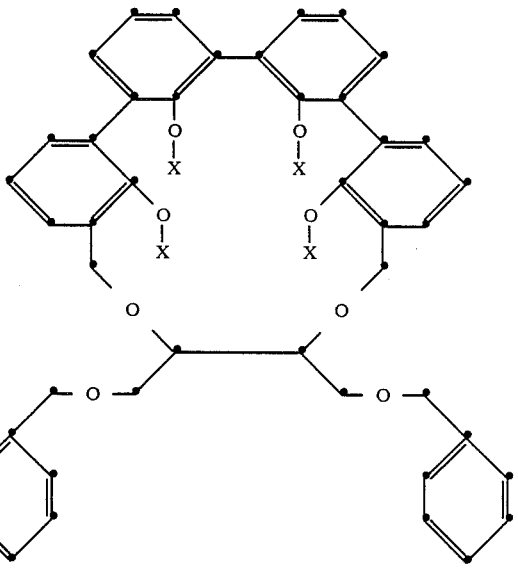
X=methyl
HS-25
X=methyl

HS-26

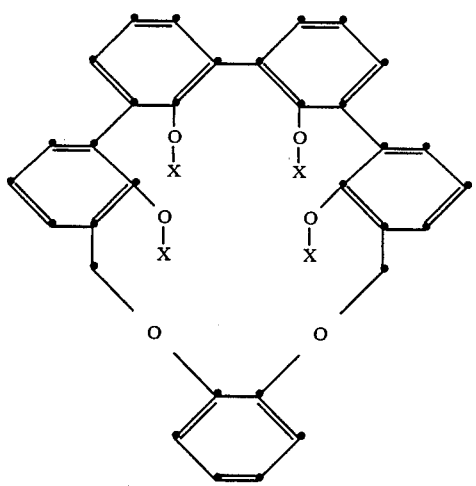

X=methyl

HS-27

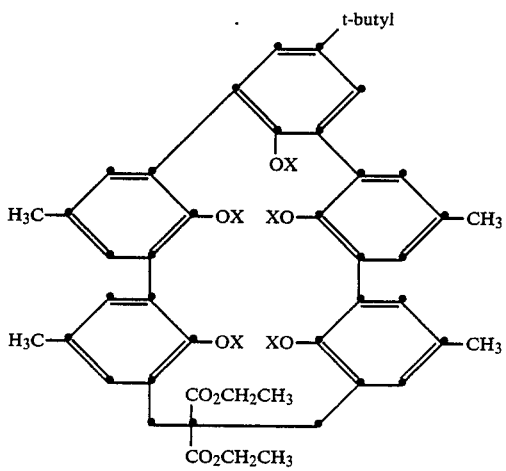

X=methyl

Among preferred hemispherands are HS-7, HS-8, HS-9, HS-18, HS-21, HS-23, HS-24, HS-26 and HS-27 with HS-21 being most preferred.

The hemispherands which are useful in the compositions of the present invention are made using methods which are known in the art or by modification of such methods which would be apparent to those of skill in the art. The procedure of Cram et al., *Journal of the American Chemical Society*, 101, pp. 3553–66 (1979), is useful. By the appropriate variation of starting materials and other reagents, a wide variety of hemispherands are made.

In many embodiments, it is desirable that the hemispherand be able not only to transport an ion across a membrane but to do so selectively; that is, the hemispherand desirably is able to transport one ion in solution in preference to other ions which might also be present in the same solution. In preferred embodiments, the hemispherand is selective for one metal ion, usually an alkali metal, in preference to a second metal ion. For example, in body fluids such as blood serum and urine, both potassium and sodium are present and it is necessary to measure the concentration of one, independent of the concentration of the other.

One particularly useful measure of the selectivity of a compound such as a hemispherand is the $\Delta\Delta G$. The $\Delta G$ for any particular ion is the free energy of complexation when that ion complexes with the hemispherand. The $\Delta\Delta G$ is the difference between the $\Delta G$ for one ion and the $\Delta G$ for the second ion. We have found that a hemispherand is capable of selectively transporting a first ion in preference to a second ion in an ion-selective membrane if the $\Delta G$ of complexation with the first ion is at least 0.3 Kcal/mole greater than the $\Delta G$ of complexation with said second ion; that is, the $\Delta\Delta G$ is at least 0.3. In particularly preferred embodiments, the $\Delta\Delta G$ is at least 0.5 Kcal/mole for sodium in preference to potassium. Hemispherands HS-1, HS-4, HS-5, HS-6, HS-7, HS-8, HS-9, HS-15, HS-18, HS-21, HS-22, HS-23, HS-24, HS-26 and HS-27 also meet this criteria.

The free energies of complexation referred to herein are measured by the method described by Dr. Cram and his coworkers (Timko et al, *J. Amer. Chem. Soc.*, 99, 4207 (1977); Newcomb and Cram, *J. Amer. Chem. Soc.*, 97, 1257 (1975); Moore et al, *J. Amer. Chem. Soc.*, 99, 6398 (1977); Helgeson et al, *J. Amer. Chem. Soc.*, 101, 4928 (1979)). Salts of the ion of interest are distributed between an aqueous and an organic phase in the absence and presence of the hemispherand. The amount of ion in any particular solution is determined by UV or NMR spectroscopy. Using this data, the amount of ion which is drawn into the organic phase by the hemispherand is determined which is related to the association constant $K_a$ for the ion and the hemispherand. The free energy of complexation is then obtained by the formula $\Delta G = -RT \ln K_a$. (R is the gas constant and T is the absolute temperature.) If the $K_a$ for a given ion is calculated relative to a reference ion, the $\Delta\Delta G$ for reference ion in preference to the given ion is simply $-RT \ln 1/K_a$. The values for $\Delta G$ herein are in Kcal/mole at 25° C. measured with $CDCl_3$ saturated with $D_2O$.

In addition to the lipophilic hemispherand, the compositions of the present invention include a compound which is capable of solvating the hemispherand. Solvation is necessary so that the ion is transported through the membrane by the solvated hemispherand. In some embodiments, one or more polymeric binders which are capable of solvating the hemispherand are used. If the polymer is capable of dissolving, at least partially, the hemispherand, it is useful in this embodiment. Exemplary polymers which are so useful are described in U.S. Pat. No. 3,419,634 (issued December 31, 1968 to Vaughn, Jr.). The preparation of ion-selective membranes using these solvating polymers is described in U.S. Pat. No. 3,743,588 (issued July 3, 1973 to Brown, Jr. et al). In these embodiments, the polymer functions as both the compound which is capable of solvating the hemispherand and the supporting matrix for the composition.

In other and preferred embodiments, the hemispherand is solvated by one or more separate organic solvents and the supporting matrix is a separate component. Such a matrix must allow for the transport of the ion which is bound to the hemispherand in the organic solvent. For example, a porous glass support is useful as the supporting matrix. In these embodiments, the hemispherand is dissolved in the organic solvent and then the resulting solution is imbibed into the porous glass support to provide an ion-selective membrane. In other embodiments, the solution of the hemispherand is dispersed in a hydrophobic binder. By "hydrophobic" is meant substantially water-insoluble. The binder dispersion is coated and dried to produce an ion-selective membrane according to the present invention.

Where a separate solvent is used to solvate the hemispherand, the solvent can be any of a wide variety of solvents, provided that it is capable of at least partially dissolving the hemispherand. The solvent (sometimes referred to in the art as a carrier solvent) provides ion mobility in the membrane. If a hydrophobic binder is used as the supporting matrix, the solvent must be compatible with the binder. Useful carrier solvents are hydrophobic organic solvents including phthalates, sebacates, aromatic and aliphatic ethers, phosphates, mixed aromatic aliphatic phosphonates, adipates, nitrated ethers or esters and mixtures of these solvents. Particularly useful solvents include dibutyl sebacate, bromophenyl phenyl ether, bis(2-ethylhexyl) sebacate, bis(2-ethylhexyl) 4-nitrophthalate, o-nitrophenyl valerate, dioctylphenyl phosphonate, o-nitrophenyl phenyl ether, o-nitrophenyl octyl ether, triisodecyl trimellitate, dimethyl phthalate, diisodecyl phthalate and tris(2-ethylhexyl) phosphate.

If the hemispherand is included in a carrier solvent as described above, a membrane is formed using a dispersion of the solvent-hemispherand in one or more binders as the supporting matrix. Useful binders include hydrophobic natural or synthetic polymers capable of forming thin films of sufficient permeability to produce, in combination with the hemispherands and carrier solvent, ionic mobility across the membrane. Useful polymers include poly(vinyl chloride); poly(vinylidene chloride); poly(acrylonitrile); polyurethanes, particularly aromatic polyurethanes; copolymers of vinyl chloride and vinylidene chloride; poly(vinyl butyral); poly(vinyl formal); poly(vinyl acetate); silicone elastomers; and copolymers of vinyl alcohol, cellulose esters and polycarbonates. Other useful polymers include carboxylated polymers of poly(vinyl chloride) and mixtures and copolymers of these materials. Membranes including binders, hemispherands and carrier solvents are prepared using conventional film-coating or casting techniques.

The membranes of the present invention contain the described components over a wide range of concentrations or coverages. The coverage of hemispherand depends upon the particular hemispherand used and the compound used to solvate it, as well as other factors. The preferred membranes comprise a hydrophobic binder having the solvent and hemispherand dispersed therein. In these membranes, hemispherand coverages of between about 0.1 g/m$^2$ and 2.0 g/m$^2$ are useful and coverages between 0.2 g/m$^2$ and 0.8 g/m$^2$ are preferred.

The carrier solvent is present in an amount sufficient to solvate the hemispherand. The amount therefore depends on the particular solvent and hemispherand chosen. Generally, more solvent is used than is necessary to solvate the hemispherand so that it remains solvated under a variety of storage conditions. A 100 percent or 500 percent excess on a weight basis is useful. Usually, the coverage of carrier solvent will be within the range of about 2 g/m$^2$ to 24 g/m$^2$.

The amount of hydrophobic binder which is present is determined by the desired thickness of the membrane and by the necessity for providing support for the hemispherand-solvent dispersion. The membranes generally have a thickness in the range of from about 2 μm to about 20 μm. The binder coverage is usually between about 2 and 24, and preferably from about 3 to about 12 g/m$^2$.

In addition to the binder, hemispherand and solvent, the membranes of the present invention optionally contain other components such as surfactants and plasticizers in amounts known to those skilled in the art.

As noted, surfactants are useful components of the described membranes. The surfactants serve a variety of functions including improving the coatability of the membrane composition and improving the solvation of the hemispherand by the binder or solvent. Useful surfactants include nonionic surfactants such as the alkylaryl polyether alcohols (Tritons TM) available from Rohm and Haas Co; (p-isononylphenoxy)polyglycidol (Surfactant 10G TM) available from Olin Mathieson Corp; polyoxyethylene (20) oleyl ether (Brij 98 TM), polyoxyethylene sorbitan monolaurate (Tween 20 TM) and Span 80 TM, all available from Atlas Chemical Industries; poly(dimethyl-co-methylphenyl siloxane) (DC-510 TM) available from Dow Corning; Zonyl FSN TM available from E. I. duPont; and fluorochemical surfactant FC134 TM available from 3M Co.

A useful ion-selective electrode comprises:
 (a) a reference electrode in contact with
 (b) a reference composition which is, in turn, in contact with one side of
 (c) an ion-selective membrane of the type described hereinabove.

In one embodiment, the ion-selective electrode is in the form of a glass tube. The ion-selective membrane forms the bottom of the tube. The tube is at least partially filled with a salt solution of known concentration forming the reference composition. Immersed in the reference composition is a reference electrode which is a metal electrode having a thin metal salt layer on its outer surface. The ion-selective electrode is used by immersing at least the membrane of the electrode in the unknown solution. One side of a voltmeter is connected to the reference electrode immersed in the reference composition and the other side is connected to a conducting probe in the unknown solution. The potential which develops across the voltmeter is proportional to the difference in ion concentration between the unknown solution and the reference composition.

The membranes of the present invention are useful in a variety of electrode structures. For example, the membranes of the present invention are useful in place of, or in addition to, the glass ion-selective membrane of a conventional barrel-type electrode. Useful electrodes of this type are disclosed, for example, in U.S. Pat. Nos. 3,598,713, 3,502,560, 3,562,129, 3,691,047, 3,753,887, 3,833,495, 3,671,414 and 3,743,588. The membranes are also useful in the ion-selective electrodes described in Japanese Patent Publication Nos. 17851/1982 and 17852/1982, both published January 29, 1982, and particularly in the dry ion-selective electrodes described therein.

In particularly preferred embodiments, the hemispherand-containing membrane of the present invention is used in a dry-operative ion-selective electrode as described in U.S. Pat. No. 4,214,968 noted hereinabove. In this embodiment, there is provided a dry-operative ion-selective electrode comprising:
 (a) a dried internal reference element comprising the dried residue of a solution of a salt and a hydrophilic polymeric binder in a solvent for the polymer and the salt and, (b) in contact with the reference element, a hydrophobic ion-selective membrane of predetermined uniform thickness in regions thereof intended for contact with the sample for analysis, the membrane comprising a hydrophobic binder having distributed therein a hemispherand ion carrier dissolved in a carrier solvent.

In this embodiment of the present invention, the electrodes are made by a process using components which are described in U.S. Pat. No. 4,214,968 (noted hereinabove), the disclosure of which is hereby incorporated by reference in its entirety. As used throughout this specification and in the claims, the expressions "dry-operative", "dried" and "uniform" have the meanings defined in the '968 patent.

The membranes and electrodes of this invention can be used to determine the concentration of cations, such as an alkali metal ion (e.g. lithium, sodium, potassium, etc.), in an aqueous solution, e.g. biological fluids such as blood sera and urine. Generally, a portion of such solution is brought into contact with the electrode (e.g. a dry ion-selective electrode) described hereinabove which is capable of making potentiometric measurements related to the alkali metal ion concentration. Subsequently, the difference in potential between the portion of aqueous solution and the reference electrode is measured. Preferably, a drop of the aqueous solution is spotted onto the ion-selective membrane of such electrode, but other ways of contacting the electrode with the solution are acceptable.

Preparation of a Hemispherand

This procedure is a modification of the procedure of Cram et al, referred to above. To a solution of ferric chloride (1 kg, 6 mole) in 3 liters of water was added a solution of p-cresol (115 g, 1.1 mole) in 19 liters of water. This solution was allowed to stand for 3 weeks. Filtration, followed by air-drying and titration of the solid with cyclohexane, gave crude trisphenol. A portion of the crude trisphenol was dissolved in chloroform and cooled to 0° C. To this solution bromine was added dropwise. As the addition neared completion, the product crystallized from the reaction mixture. Filtration, followed by rinsing with cold chloroform, gave the pure trisphenol dibromide.

A 2 molar solution of trisphenol dibromide in acetone was refluxed with 3.2 equivalents of potassium carbonate and 3.2 equivalents of ethyl iodide. The reaction was cooled, and the solvent removed to leave a paste which was slurried in dichloromethane. The dichloromethane solution was separated from the solid, dried over sodium sulfate, filtered and evaporated to leave the trisethoxydibromide which was used without further purification.

To a solution of the trisethoxydibromide in diethyl ether at −78° C. were added 2.2 equivalents of N,N,N′,N′-tetramethylethylenediamine (TMEDA), followed by 2.2 equivalents of 2.4 molar n-butyl lithium in hexane. The solution was stirred at −78° C. under nitrogen for 6 hours, followed by quenching with carbon dioxide gas. The mixture was allowed to warm to 0° C. and acidified with concentrated hydrochloric acid. The mixture was extracted twice with a 1:1 solution of ethyl acetate in ethyl ether. The combined organic layers were dried over sodium sulfate, filtered and evaporated to leave the crude product, the trisethoxydiacid, which was purified by trituration with hexane.

To a stirred solution of the trisalkoxydiacid in dry tetrahydrofuran (THF) was added 3 equivalents of $BH_3.THF$. The mixture was refluxed for 3 hours, then cooled to room temperature. Water was added, followed by a large excess of saturated potassium carbonate. The mixture was stirred, then extracted twice with ether. The combined organic layers were washed with water and brine, then dried over sodium sulfate plus magnesium sulfate. The solvent was removed to yield the product, a trisethoxybishydroxymethyl compound, which was used without further purification.

One equivalent of phosphorus tribromide was added to an anhydrous benzene solution of the desired trisalkoxybishydroxymethyl compound and stirred under nitrogen for 24 hours. The mixture was partitioned between saturated sodium bicarbonate and diethyl ether. The organic layer was washed with saturated sodium bicarbonate, water and brine, then dried over sodium sulfate and magnesium sulfate, filtered and evaporated. The crude product was purified by flash chromatography on silicon dioxide with a 1:1 solution of hexane and dichloromethane.

The final hemispherand product was prepared in the following manner. A solution containing both the trisalkoxybisbromomethyl compound and dry diethylene glycol was added with a constant addition funnel to a refluxing solution of 2.2 equivalents of sodium hydride in dry tetrahydrofuran over a 24-hour period. Refluxing was continued for 8 hours; then the reaction was cooled to room temperature and carefully quenched with water. The solvent was removed and the residue was partitioned between water and dichloromethane. The organic layer was dried over sodium sulfate and magnesium sulfate and evaporated. The crude hemispherand which resulted was subjected to gel permeation chromatography to separate the desired product from oligomeric material. HS-1 was obtained having a mp of 160.5°–162° C. The structure was confirmed by NMR, mass spectrum, elemental analysis and X-ray analysis.

In a similar manner, the corresponding oil propoxy (HS-2) and solid isopropoxy (HS-3), mp=164°–166° C., were prepared. The structures were confirmed by NMR, mass spectrum and elemental analysis.

Electrode Format

Ion-selective electrodes were prepared using a variety of hemispherands described above, as well as a comparative compound. The electrodes were of the format and were prepared by the methods described in U.S. Pat. No. 4,214,968 referenced above. Each electrode comprised a polyester support having layers in sequence as follows: silver/silver chloride reference electrode; electrolyte layer comprising gelatin (3–6 $g/m^2$, NaCl (1.5–3.5 $g/m^2$), glycerol (0.25–0.4 $g/m^2$) and Olin Surfactant 10G ™ (0.3–0.9 $g/m^2$); and the membrane layer.

The membrane layer contained: 1.8% carboxylated poly(vinyl chloride) binder (3.0–6.0 $g/m^2$), a carrier solvent as indicated (4–8 $g/m^2$), the hemispherand or a comparative compound as indicated, and the surfactant DC-510 ™ (0.03–0.09 $g/m^2$).

The following examples are presented.

EXAMPLES 1–16

A hemispherand and a carrier solvent were incorporated in the membrane layer of an electrode as described above. The electrodes were tested by spotting 10 μL aliquots of solutions containing 0.05, 0.10, 0.15 or 0.30M sodium chloride and 0.10M KCl, LiCl, NH4Cl, CaCl2 or MgCl2 onto samples of the electrode. Potentials were measured against a silver/silver chloride electrode. The potential developed for each aliquot was plotted against the concentration of sodium in the aliquot. The result was a Nernstian slope in the range of $10^{-4}$ to $10^{-1}$M sodium for each experiment.

For each experiment, the selectivity coefficients (k) for each of the cations other than sodium were calculated (sodium being defined as one) using the potential data from the appropriate aliquot. The results are shown in Table 1. Making the assumption that ionic mobilities of the ion complex in the membrane are not appreciably different, then the selectivity coefficient Ka is related to the $\Delta\Delta G$ by the following formula: $\Delta\Delta G = -RT \ln 1/Ka$. In the table, BEHS is bis(2-ethylhexyl) sebacate, DIDP is diisodecyl phthalate, ONPV is o-nitrophenyl valerate and NPOE is o-nitrophenyl octyl ether. In Example 1, the $\Delta\Delta G$ for Na+ over K+ is $-RT \ln 1/0.36$ which is equal to 0.6 Kcal. A $\Delta\Delta G$ of 0.3 Kcal corresponds to a K of 0.7.

TABLE 1

| Example | Hemi-spherand | Solvent | Selectivity Coefficients | | | | | |
|---|---|---|---|---|---|---|---|---|
| | | | Na+ | K+ | Li+ | NH4+ | Ca++ | Mg++ |
| 1 | HS-1 | BEHS | 1 | 0.36 | 0.006 | 0.009 | 0.006 | 0.0004 |
| 2 | HS-2 | BEHS | 1 | 0.52 | 0.003 | 0.014 | 0.017 | 0.001 |
| 3 | HS-5 | BEHS | 1 | 0.14 | 0.004 | 0.009 | 0.022 | 0.002 |
| 4 | HS-6 | BEHS | 1 | 0.13 | 0.003 | 0.006 | 0.006 | 0.0007 |
| 5 | HS-7 | BEHS | 1 | 0.05 | 0.005 | 0.006 | 0.008 | 0.0005 |
| 6 | HS-4 | BEHS | 1 | 0.32 | 0.17 | 0.008 | 0.013 | 0.0004 |
| 7 | HS-20 | BEHS | 1 | 0.58 | 0.004 | 0.015 | 0.001 | 0.0006 |
| 8 | HS-21 | BEHS | 1 | 0.011 | 0.004 | 0.003 | 0.006 | 0.0008 |
| 9 | HS-22 | BEHS | 1 | 0.12 | 0.004 | 0.009 | 0.006 | 0.0001 |
| 10 | HS-23 | BEHS | 1 | 0.008 | 0.006 | 0.001 | 0.005 | 0.00008 |
| 11 | HS-24 | BEHS | 1 | 0.02 | 0.005 | 0.002 | 0.007 | 0.0003 |
| 12 | HS-25* | BEHS | .005 | 1 | 0.003 | 0.09 | 0.0005 | 0.0002 |
| 13 | HS-2 | NPOE | 1 | 0.53 | 0.005 | 0.01 | 0.007 | 0.0007 |
| 14 | HS-7 | NPOE | 1 | 0.06 | 0.004 | 0.004 | 0.006 | 0.0006 |
| 15 | HS-7 | ONPV | 1 | 0.09 | 0.009 | 0.009 | 0.008 | 0.003 |
| 16 | HS-27 | DIDP | 1 | 0.09 | 0.06 | 0.05 | NA | NA |

*K+ selective
NA = not available

The fact that each ion-selective electrode exhibited a Nernstian potential plot over a wide range of sodium concentration establishes that each of the hemispherands is functioning as a transporter of ions. The selectivity of these particular hemispherands for sodium is established by the fact that each of the other ions tested exhibited a selectivity coefficient less than 1.

Comparative Example

Example 1 was repeated except that a spherand was substituted for the hemispherand in the membrane layer. The spherand had the structure:

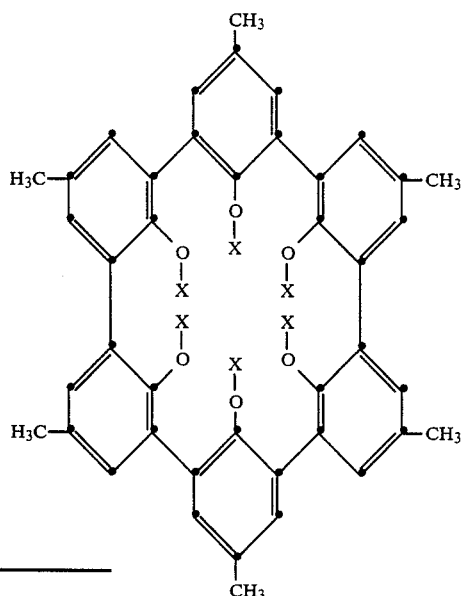

X = CH3

A plot of the potential vs. the concentration of sodium in the aliquot showed no response.

Although the invention has been described in considerable detail with particular reference to certain preferred embodiments thereof, variations and modifications can be effected within the spirit and scope of the invention.

We claim:

1. A composition comprising a lipophilic hemispherand compound, a compound capable of solvating the hemispherand compound, and a supporting matrix.

2. The composition of claim 1 wherein said solvating compound is a hydrophobic carrier solvent.

3. The composition claim 1 wherein said hemispherand is represented by the structural formula:

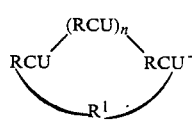

wherein n is an integer of from 1 to 3; each RCU is a rigid cyclic unit individually selected from the group consisting of units of the structure:

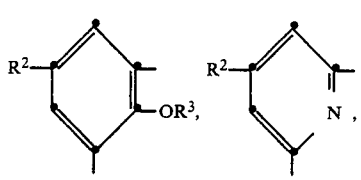

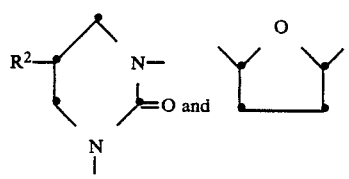

wherein:
R² is hydrogen or a group selected from alkyl, alkenyl, cycloalkyl, aryl and alkyl, alkenyl, cycloalkyl and aryl groups containing heteroatoms or containing heteroatom substituents;
R³ is an alkyl or alkenyl group or, when taken together with an R³ group from another RCU, forms an alkylene group or an alkylene group interrupted with heteroatoms; and
R¹ represents the atoms necessary to complete a macrocyclic ring structure, with the proviso that R¹ contains (a) at least one coordinating site for ions and (b) at least two alkylene groups as part of the ring structure.

4. The composition of claim 3 wherein n is 1 or 2.

5. The composition of claim 3 wherein said hemispherand compound is selected from the group consisting of HS-7, HS-8, HS-9, HS-18, HS-21, HS-23, HS-24, HS-26 and HS-27.

6. An ion-selective membrane composition capable of, when contacted with a solution containing first and second ions, selectively transporting said first ion in preference to said second ion, said composition comprising a hemispherand ionophore, a compound capable of solvating said ionophore, and a supporting matrix, wherein the hemispherand ionophore has a ΔG of complexation with said first ion which is at least 0.3 Kcal/mole greater than the ΔG of complexation with said second ion.

7. The composition of claim 6 wherein said first ion is sodium and said second ion is potassium.

8. The composition of claim 7 wherein said hemispherand has a ΔG of complexation with sodium which is at least 0.5 Kcal/mole greater than the ΔG of complexation with potassium.

9. An ion-selective electrode having an ion-selective membrane composition comprising an ionophore which is a lipophilic hemispherand compound, a compound capable of solvating said hemispherand compound and a supporting matrix.

10. An ion-selective electrode comprising:
(a) a reference electrode in contact with
(b) a reference composition which is, in turn, in contact with one side of
(c) an ion-selective membrane composition comprising an ionophore which is a hemispherand compound, a compound capable of solvating said hemispherand compound, and a supporting matrix.

11. The electrode of claim 10 wherein said hemispherand is represented by the structural formula:

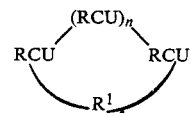

wherein n is an integer of from 1 to 3; each RCU is a rigid cyclic unit individually selected from the group consisting of units of the structure:

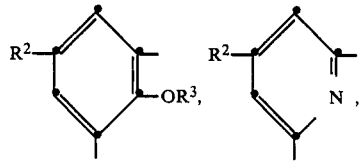

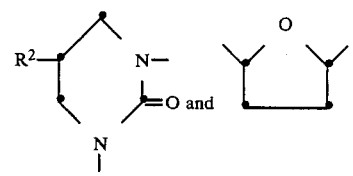

wherein:
R² is hydrogen or a group selected from alkyl, alkenyl, cycloalkyl, aryl and alkyl, alkenyl, cycloalkyl and aryl groups containing heteroatoms or containing heteroatom substituents;
R³ is an alkyl or alkenyl group or, when taken together with an R³ group from another RCU, forms an alkylene group or an alkylene group interrupted with heteroatoms; and
R¹ represents the atoms necessary to complete a macrocyclic ring structure, with the proviso that R¹ contains (a) at least one coordinating site for ions and (b) at least two alkylene groups as part of the ring structure.

12. The electrode of claim 11 wherein said hemispherand compound is selected from the group consisting of HS-7, HS-8, HS-9, HS-18, HS-21, HS-23, HS-24, HS-26 and HS-27.

13. The electrode of claim 10 wherein the compound capable of solvating the hemispherand compound is selected from the group consisting of phthalates, sebacates, aromatic and aliphatic ethers, phosphates, mixed aromatic-aliphatic phosphonates, adipates, nitrated ethers or esters, and mixtures thereof.

14. The electrode of claim 10 wherein said supporting matrix is porous glass.

15. The electrode of claim 10 wherein said supporting matrix is a hydrophobic binder.

16. The electrode of claim 10 comprising a surfactant.

17. A dry-operative ion-selective electrode comprising a lipophilic hemispherand ionophore dissolved in a compound capable of solvating said hemispherand compound.

18. The electrode of claim 17 wherein said ionophore and solvating compound are distributed within a hydrophobic binder.

19. A dry-operative ion-selective electrode comprising:

(a) a dried internal reference element comprising the dried residue of a solution of a salt and a hydrophilic polymeric binder in a solvent for the polymer and the salt and, (b) in contact with said reference element, a hydrophobic ion-selective membrane of predetermined uniform thickness in regions thereof intended for contact with a sample for analysis, the membrane comprising a hydrophobic polymer binder having distributed therein a lipophilic hemispherand ionophore dissolved in a compound capable of solvating said hemispherand compound, which solvating compound is a hydrophobic carrier solvent.

20. The electrode of claim 19 wherein said hemispherand is represented by the structural formula:

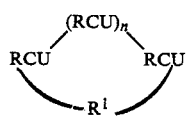

wherein n is an integer of from 1 to 3; each RCU is a rigid cyclic unit individually selected from the group consisting of units of the structure:

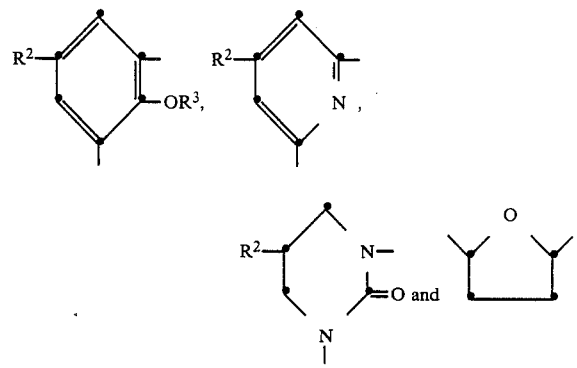

wherein:
$R^2$ is hydrogen or a group selected from alkyl, alkenyl, cycloalkyl, aryl and alkyl, alkenyl, cycloalkyl and aryl groups containing heteroatoms or containing heteroatom substituents;

$R^3$ is an alkyl or alkenyl group or, when taken together with an $R^3$ group from another RCU, forms an alkylene group or an alkylene group interrupted with heteroatoms; and $R^1$ represents the atoms necessary to complete a macrocyclic ring structure, with the proviso that $R^1$ contains (a) at least one coordinating site for ions and (b) at least two alkylene groups as part of the ring structure.

21. The electrode of claim 20 wherein n is 1 or 2.

22. The electrode of claim 20 wherein said hemispherand compound is selected from the group consisting of HS-7, HS-8, HS-9, HS-18, HS-21, HS-23, HS-24, HS-26 and HS-27.

* * * * *